(12) United States Patent
Bette et al.

(10) Patent No.: US 8,664,415 B2
(45) Date of Patent: Mar. 4, 2014

(54) PROCESS FOR PREPARING (METH)ACRYLATES OF $C_{17}$-ALCOHOL MIXTURES

(75) Inventors: Virginie Bette, Mannheim (DE); Jochen Petzoldt, Weisenheim am Berg (DE); Boris Breitscheidel, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 178 days.

(21) Appl. No.: 12/952,732

(22) Filed: Nov. 23, 2010

(65) Prior Publication Data

US 2011/0130582 A1 Jun. 2, 2011

Related U.S. Application Data

(60) Provisional application No. 61/264,704, filed on Nov. 27, 2009.

(30) Foreign Application Priority Data

Nov. 27, 2009 (DE) .................. 10 2009 047 228

(51) Int. Cl.
*C09F 7/00* (2006.01)

(52) U.S. Cl.
USPC ........................................... 554/26

(58) Field of Classification Search
USPC ........................................... 554/26
See application file for complete search history.

(56) References Cited

U.S. PATENT DOCUMENTS

| | | | |
|---|---|---|---|
| 6,818,791 B2 * | 11/2004 | Martin et al. ............... | 560/205 |
| 6,927,267 B1 * | 8/2005 | Varela de la Rosa et al. | 526/287 |
| 2004/0019235 A1 | 1/2004 | Martin et al. | |
| 2004/0024241 A1 | 2/2004 | Martin et al. | |
| 2010/0317887 A1 | 12/2010 | Meisenburg et al. | |

FOREIGN PATENT DOCUMENTS

| | | |
|---|---|---|
| DE | 2 317 226 | 10/1974 |
| DE | 199 41 136 A1 | 3/2001 |
| DE | 100 63 175 A1 | 6/2002 |
| EP | 1 342 762 A2 | 9/2003 |
| EP | 1 923 454 A1 | 5/2008 |
| JP | 5-70404 | 3/1993 |
| JP | 11-80082 | 3/1999 |
| WO | WO 02/50014 A1 | 6/2002 |
| WO | WO 02/50015 A1 | 6/2002 |
| WO | WO 02/055472 A1 | 7/2002 |
| WO | WO 2009/106550 A1 | 9/2009 |
| WO | WO 2009/124979 A1 | 10/2009 |
| WO | WO 2009124979 A1 * | 10/2009 |

OTHER PUBLICATIONS

International Search Report issued Apr. 1, 2011, in International Patent Application no. PCT/EP2010/067986.
U.S. Appl. No. 13/236,893, filed Sep. 20, 2011, Bette, et al.
R. Billet, "III. Auslegung Der Verdampferanlagen", Verdampfertechnik [Evaporator Technology], HTB-VERLAG, Bibliographisches Institut Mannheim, 1965, pp. 52-55.
"Liquid—Liquid Extraction—Apparatus", Ullmann's Encyclopedia of Industrial Chemistry, 6th Edition, 1999 (Electronic Release, no longer available).

* cited by examiner

*Primary Examiner* — Deborah D Carr
(74) *Attorney, Agent, or Firm* — Oblon, Spivak, McClelland, Maier & Neustadt, L.L.P.

(57) ABSTRACT

A process for preparing (meth)acrylates of $C_{17}$-alcohol mixtures by reacting (meth)acrylic acid with a $C_{17}$-alcohol mixture in the presence of at least one acidic catalyst and of at least one polymerization inhibitor and in the presence of a solvent which, with water, forms an azeotrope in which the esterification is performed in a reactor with a circulation evaporator, the azeotrope is distilled off and condensed, and the condensate splits into an aqueous phase and an organic phase, wherein the $C_{17}$-alcohol mixture has a mean degree of branching (iso index) of 2.8 to 3.7.

9 Claims, No Drawings

PROCESS FOR PREPARING (METH)ACRYLATES OF $C_{17}$-ALCOHOL MIXTURES

The present invention relates to a process for batchwise preparation of (meth)acrylates of $C_{17}$-alcohol mixtures by esterifying (meth)acrylic acid with $C_{17}$-alcohol mixtures having a mean degree of branching (iso index) of 2.8 to 3.7.

In this document, the term "(meth)acrylic acid" is abbreviated notation for methacrylic acid and/or acrylic acid, (meth)acrylic ester is abbreviated notation for methacrylic ester and/or acrylic ester, and (meth)acrylate is abbreviated notation for methacrylate and/or acrylate.

The polymers or copolymers prepared on the basis of (meth)acrylates of $C_{17}$-alcohol mixtures are of great economic significance in the form of polymer dispersions. They find use, for example, as adhesives, paints or textile, leather and papermaking assistants.

The preparation of relatively highly alkylated (meth)acrylates by acid-catalyzed esterification of (meth)acrylic acid with $C_8$-$C_{20}$-monoalcohols is already known and is described, for example, in WO 2002/050014 A1 and WO 2002/050015 A1.

German published specification DE 2 317 226 A1 discloses a process for preparing (meth)acrylic esters from a mixture of $C_{10}$-$C_{18}$-alcohols by titanium-catalyzed transesterification of (meth)acrylic acid. According to this, the esterification is effected in the presence of a combination of 2,6-di-tert-butylparacresol (TBC) and adsorptive charcoal as polymerization inhibitors. The titanium alkoxide used as the catalyst is hydrolyzed at the elevated temperature and filtered off together with the charcoal.

Japanese published specification JP 11-80082 A discloses the esterification of (meth)acrylic acid with $C_8$-$C_{22}$-alcohol in the presence of acidic catalysts, for example p-toluenesulfonic acid and methanesulfonic acid.

The transesterification of methyl methacrylate with long-chain $C_3$-$C_{20}$-alcohols is described in Japanese published specification JP 05 070404. According to this, this transesterification is effected in the presence of potassium oxide or hydroxide, magnesium oxide or hydroxide or sodium oxide or hydroxide as the catalyst.

In addition, the esterification of (meth)acrylic acid with straight-chain, saturated or unsaturated $C_8$-$C_{22}$-fatty alcohols has been described, wherein the long-chain fatty alcohols are purified prior to the esterification by distillation over sodium boronate.

None of the documents cited explicitly discloses the preparation of (meth)acrylates of $C_{17}$-alcohols. More particularly, the use of a $C_{17}$-alcohol mixture which has a mean degree of branching of 2.8 to 3.7 is not disclosed. The degree of branching of the $C_{17}$-alcohol mixture and consequently also of the resulting (meth)acrylic esters is of particular significance for the use of the (meth)acrylic esters as monomers and comonomers for preparation of (co)polymers for different industrial applications, since monomers and comonomers having not too high a degree of branching should preferably be used. Instead, the aforementioned documents relate essentially to the synthesis of $C_{16}$-, $C_{18}$- and $C_{20}$-alkyl(meth)acrylates.

It was therefore an object of the present invention to provide a process for preparing (meth)acrylates of $C_{17}$-alcohol mixtures which have not too high a mean degree of branching, with which the (meth)acrylates are obtained from $C_{17}$-alcohol mixtures in high yields and in high purities. Moreover, products with low color numbers should be the result.

The object is achieved by a process for preparing (meth)acrylates of $C_{17}$-alcohol mixtures by reacting (meth)acrylic acid with a $C_{17}$-alcohol mixture in the presence of at least one acidic catalyst and of at least one polymerization inhibitor and in the presence of a solvent which, with water, forms an azeotrope wherein the esterification is performed in a reactor with a circulation evaporator, the azeotrope is distilled off and condensed, and the condensate splits into an aqueous phase and an organic phase, and wherein the $C_{17}$-alcohol mixture has a mean degree of branching (iso index) of 2.8 to 3.7.

In the process according to the invention, $C_{17}$-alcohol mixtures which have a mean degree of branching (iso index) of 2.8 to 3.7 are used. The $C_{17}$-alcohol mixtures preferably have a mean degree of branching of 2.9 to 3.6, preferably of 3.01 to 3.5 and especially of 3.05 to 3.4. The $C_{17}$-alcohol mixtures most preferably have a mean degree of branching in the region of about 3.1.

The mean degree of branching of the $C_{17}$-alcohol mixture and consequently also of the resulting (meth)acrylic esters is essential to the invention since not too high a mean degree of branching is important for the use of these (meth)acrylic esters as monomers and comonomers for preparation of (co)polymers for various industrial applications.

In the context of the invention, the degree of branching is defined as the number of methyl groups in a molecule of the alcohol minus 1. The mean degree of branching is the statistical mean of the degrees of branching of the molecules of a sample. The mean degree of branching can be determined by $^1$H NMR spectroscopy as follows: to this end, a sample of the alcohol or alcohol mixture is first subjected to a derivatization with trichloroacetyl isocyanate (TAI). This converts the alcohols to the carbamic esters.

The signals of the primary alcohols esterified in this way are at $\delta=4.7$ to 4.0 ppm, those of esterified secondary alcohols (where present) at about 5 ppm, and water present in the sample reacts with TAI to give the carbamic acid. All methyl, methylene and methine protons are in the range from 2.4 to 0.4 ppm. The signals <1 ppm are assigned to the methyl groups. From the spectrum thus obtained, it is possible to calculate the mean degree of branching (iso index) as follows:

$$\text{iso index} = ((F(CH_3)/3)/(F(CH_2-OH)/2))-1$$

where $F(CH_3)$ is the signal area corresponding to the methyl protons and $F(CH_2-OH)$ is the signal area of the methylene protons in the $CH_2$—OH group.

The $C_{17}$-alcohol mixture preferably has a content of alcohols having 17 carbon atoms of at least 95% by weight, more preferably at least 98% by weight, especially at least 99% by weight, based on the total weight of the $C_{17}$-alcohol mixture. The $C_{17}$-alcohol mixture is especially one which consists essentially (i.e. to an extent of more than 99.5% by weight, especially to an extent of more than 99.9% by weight) of alcohols having 17 carbon atoms.

For preparation of such $C_{17}$-alcohol mixtures, reference is made here to the published specification WO 2009/124979 A1 and the literature cited therein.

What is advantageous about the above-described $C_{17}$-alcohol mixtures is that they have a high purity of at least 95% by weight and a mean degree of branching of 2.8 to 3.7. The process according to the invention for preparing (meth)acrylic esters therefore likewise affords $C_{17}$-alkyl(meth)acrylates with a high purity. $C_{17}$-Alkyl(meth)acrylates obtainable commercially to date are typically mixtures of $C_{16}$- and $C_{18}$-alkyl (meth)acrylates. As a result, the mixing and isomer ratios in different batches may be different. To date, this has had an adverse effect on the properties of the resulting (co)polymers.

A particularly advantageous feature in this context is the low solidification point of the (meth)acrylic esters of $C_{17}$- alcohol mixtures prepared by the process according to the invention. Owing to the high purity and the constant degree of branching, the solidification point (at atmospheric pressure) is below 0° C., preferably below −20° C. and more preferably below −40° C. In contrast, the above-described $C_{17}$-alkyl (meth)acrylates obtainable commercially to date have a solidification point (at atmospheric pressure) of above 0° C.

The process according to the invention is advantageous since a high degree of esterification is attained and high yields are achieved. In addition, no significant polymer formation occurs in the course of esterification or workup, and the end product is substantially colorless.

The water formed in the esterification, which forms an azeotrope with the solvent, is discharged via a column attached to the reactor and condensed.

The condensate obtained (azeotrope) splits into an aqueous phase, which is discharged and advantageously worked up (reextraction of the acid present), and a solvent phase, which is recycled as reflux into the column and if appropriate partly into the reactor and/or evaporator, as described in DE 199 41 136 A1 and DE 100 63 175 A1.

A reextraction of the (meth)acrylic acid present is preferably effected with the solvent used as the extractant, for example with cyclohexane at a temperature between 10 and 40° C. and a ratio of aqueous phase to extractant of 1:5-30, preferably 1:10-20. The acid present in the extractant can preferably be conducted directly into the esterification.

After the esterification has ended, the hot reaction mixture is cooled rapidly and if appropriate diluted with solvent.

Subsequently, the solvent is removed by distillation from the target ester.

The process according to the invention consists essentially of the following stages:

1) Esterification

The esterification apparatus consists of a reactor with a circulation evaporator and an attached distillation column with condenser and phase separation vessel.

The reactor may, for example, be a reactor with jacket heating and/or internal heating coils. Preference is given to using a reactor with external heat exchanger and natural or forced circulation (using a pump). In the case of natural circulation, the cycle stream is accomplished without mechanical aids.

Suitable circulation evaporators are known to those skilled in the art and are described, for example, in R. Billet, Verdampfertechnik [Evaporator Technology], HTB-Verlag, Bibliographisches Institut Mannheim, 1965, 53. Examples of circulation evaporators are tube bundle heat exchangers, plate heat exchangers, etc.

It will be appreciated that it is also possible for a plurality of heat exchangers to be present in the circulation system.

The distillation column is of a design known per se and has the customary internals. The column internals used may in principle be all common internals, for example trays, structured packings and/or random packings. Among the trays, preference is given to bubble-cap trays, sieve trays, valve trays, Thormann trays and/or dual-flow trays; among the random packings, preference is given to those comprising rings, helices, saddles or braids.

In general, from 5 to 20 theoretical plates are sufficient.

The condenser and the separating vessel are of conventional design.

(Meth)acrylic acid and the $C_{17}$-alcohol mixture are generally used in equivalent amounts, but it is also possible to use a deficiency or excess of (meth)acrylic acid.

Both (meth)acrylic acid and (meth)acrylic esters are polymerizable compounds. Therefore, sufficient inhibition of polymerization should already be ensured in the process step of esterification. Suitable polymerization inhibitors are disclosed further down. Among the stabilizers mentioned there, especially copper(II) chloride is suitable for the esterification.

Preference is given to establishing an excess of (meth) acrylic acid per hydroxyl group (equivalent) to be esterified of 5-100 mol %, preferably 5-50 mol % and more preferably 5-10 mol %.

Useful esterification catalysts include the customary mineral acids and sulfonic acids, preferably sulfuric acid, phosphoric acid, alkylsulfonic acids (e.g. methanesulfonic acid, trifluoromethanesulfonic acid) and arylsulfonic acids (e.g. benzene-, p-toluene-, or dodecylbenzenesulfonic acid) or mixtures thereof, but acidic ion exchangers or zeolites are also conceivable.

Particular preference is given to sulfuric acid, methanesulfonic acid and p-toluene-sulfonic acid, or mixtures thereof.

They are used generally in an amount of 0.1-5% by weight, based on the esterification mixture, preferably 0.5-5% by weight and more preferably 1-4% by weight.

If required, the esterification catalyst can be removed from the reaction mixture with the aid of an ion exchanger. The ion exchanger can be added directly to the reaction mixture and then filtered off, or the reaction mixture can be passed through an ion exchanger bed.

Preference is given to leaving the esterification catalyst in the reaction mixture.

Suitable solvents for azeotropic removal of the water of reaction are in particular aliphatic, cycloaliphatic and aromatic hydrocarbons or mixtures thereof.

Preference is given to employing n-pentane, n-hexane, n-heptane, cyclohexane, methylcyclohexane, benzene, toluene or xylene. Particular preference is given to cyclohexane, methylcyclohexane and toluene.

The amount used is, for example, 10-200% by weight, preferably 20-100% by weight, more preferably 30-100% by weight, based on the sum of (meth)acrylic acid and $C_{17}$-alcohol mixture.

The reaction temperature is generally 60-140° C., preferably 70-110° C., most preferably 75-100° C. The starting temperature is generally below 100° C., preferably below 90° C. and more preferably below 80° C. In general, the end temperature of the esterification is 5-30° C. higher than the starting temperature. The temperature of the esterification can be determined and controlled by varying the solvent concentration in the reaction mixture, as described in DE 199 41 136 A1 and DE 100 63 175 A1.

The esterification can be carried out at ambient pressure or else at elevated pressure or reduced pressure; preference is given to working at standard pressure.

The reaction time is generally from 30 minutes to 10 hours, preferably 1-6 hours and more preferably 2-4 hours.

The (meth)acrylic acid and $C_{17}$-alcohol mixture reactants, and also the other components such as solvents, polymerization inhibitor (mixture) and catalyst, can be added as desired.

In a preferred embodiment, solvent and the $C_{17}$-alcohol mixture are initially charged in the reactor at least partly, preferably completely, and heated. As soon as the circulation is in operation, the remaining components (meth)acrylic acid, polymerization inhibitor (mixture) and catalyst can be metered in together or separately from one another. The metered addition is effected generally within 0.5-5 hours, continuously or in portions.

The usable (meth)acrylic acid is not restricted and may, in the case of crude (meth)acrylic acid, comprise, for example, the following components:

| | |
|---|---|
| (meth)acrylic acid | 90-99.9% by weight |
| acetic acid | 0.05-3% by weight |
| propionic acid | 0.01-1% by weight |
| diacrylic acid | 0.01-5% by weight |
| water | 0.05-5% by weight |
| aldehydes | 0.01-0.3% by weight |
| inhibitors | 0.01-0.1% by weight |
| maleic acid/anhydride | 0.001-0.5% by weight |

The crude (meth)acrylic acid used is generally stabilized with 100-600 ppm, preferably with 200-500 ppm, of one of the polymerization inhibitors mentioned below, preferably phenothiazine or hydroquinone monomethyl ether, or other stabilizers which enable comparable stabilization.

It will be appreciated that it is also possible to use glacial (meth)acrylic acid with, for example, the following purity:

| | |
|---|---|
| (meth)acrylic acid | 99.7-99.99% by weight |
| acetic acid | 50-1000 ppm by weight |
| propionic acid | 10-500 ppm by weight |
| diacrylic acid | 10-500 ppm by weight |
| water | 50-1000 ppm by weight |
| aldehydes | 1-500 ppm by weight |
| inhibitors | 1-300 ppm by weight |
| maleic acid/anhydride | 1-200 ppm by weight |

The glacial (meth)acrylic acid used is generally stabilized with 100-400 ppm, preferably with 200-300 ppm, of one of the polymerization inhibitors mentioned below, preferably phenothiazine or hydroquinone monomethyl ether, or other stabilizers which enable comparable stabilization.

The water formed in the reaction is removed from the reaction mixture continuously as an azeotrope with the solvent via the column attached to the reactor and condensed, and the condensate splits into a water phase and an organic phase.

The aqueous phase of the condensate, which generally comprises 0.1-10% by weight of (meth)acrylic acid, is removed and discharged. Advantageously, the (meth)acrylic acid present therein can be extracted with an extractant, for example with cyclohexane, at a temperature between 10 and 40° C. and a ratio of aqueous phase to extractant of 1:5-30, preferably 1:10-20, and recycled into the esterification.

The organic phase can be recycled fully or partly as reflux into the column and any excess remainder can be recycled into the reactor. A portion of this phase can, in the case of use of natural circulation, if appropriate be introduced into the heat exchanger of the circulation system of the reactor to promote the natural circulation, preferably at least 10% by weight of the organic phase, more preferably at least 15% by weight and most preferably at least 20% by weight.

An advantageous variant consists in passing the organic phase (solvent phase) into a reservoir vessel and withdrawing from this vessel the amount of solvent required in each case to maintain the reflux, for introduction into the circulation evaporator, and as the solvent for reaction and extraction.

To further promote the circulation, it is possible to pass an inert gas, preferably an oxygenous gas, more preferably air or a mixture of air and nitrogen (lean air) into the circulation system, for example in amounts of 0.1-1 m$^3$/m$^3$h, preferably 0.2-0.8 m$^3$/m$^3$h and more preferably 0.3-0.7 m$^3$/m$^3$h, based on the volume of the reaction mixture.

The course of the esterification can be monitored by monitoring the amount of water discharged and/or the decrease in the (meth)acrylic acid concentration in the reactor.

The reaction can be ended, for example, as soon as 90% of the theoretically expected amount of water has been discharged by the solvent, preferably at least 95% and more preferably at least 98%.

After the esterification has ended, the reaction mixture is cooled rapidly to a temperature of from 10 to 30° C. in a customary manner, and if appropriate a target ester concentration of 60-80% is established by adding solvent.

2) Preliminary Wash and Neutralization

The reaction mixture is, if appropriate, treated in a washing apparatus with water or a 5-30% by weight, preferably 5-20% by weight, more preferably 5-15% by weight, sodium chloride solution, potassium chloride solution, ammonium chloride solution, sodium sulfate solution or aluminum sulfate solution, preferably sodium chloride solution.

The ratio of reaction mixture:wash liquid is generally 1:0.1-1, preferably 1:0.2-0.8, more preferably 1:0.3-0.7.

The wash can be carried out, for example, in a stirred vessel or in another conventional apparatus, for example in a column or mixer-settler apparatus.

In terms of process technology, for a wash in the process according to the invention, it is possible to use all extraction processes, extraction apparatus, washing processes and washing apparatus known per se, for example those which are described in Ullmann's Encyclopedia of Industrial Chemistry, 6th ed, 1999 Electronic Release, chapter: Liquid—Liquid Extraction—Apparatus. For example, they may be single-stage or multistage, preferably single-stage, extractions, and also those in cocurrent or countercurrent mode.

The preliminary wash is preferably used when (some of) the inhibitors used are metal salts, preferably copper or copper salts.

The organic phase of the preliminary wash, which still comprises small amounts of catalyst and the majority of excess (meth)acrylic acid, is neutralized with a 5-25% by weight, preferably 5-20% by weight, more preferably 5-15% by weight, aqueous solution of a base, for example sodium hydroxide solution, potassium hydroxide solution, sodium hydrogencarbonate, sodium carbonate, potassium hydrogencarbonate, calcium hydroxide, aqueous ammonia or potassium carbonate, to each of which may if appropriate be added 5-15% by weight of sodium chloride, potassium chloride, ammonium chloride or ammonium sulfate, preferably neutralized with sodium hydroxide solution or sodium hydroxide/sodium chloride solution.

The base is added in such a way that the temperature in the apparatus does not rise above 35° C., and is preferably between 20 and 35° C., and the pH is 10-14. The heat of neutralization is removed, if appropriate, by cooling the vessel with the aid of internal cooling coils or by means of jacket cooling.

The ratio of reaction mixture:neutralization liquid is generally 1:0.1-1, preferably 1:0.2-0.8, more preferably 1:0.3-0.7.

With regard to the apparatus, the same applies as was stated above.

Optionally, to remove base or salt traces from the neutralized reaction mixture, a subsequent wash may be advantageous, which can be carried out analogously to the preliminary wash.

3) Solvent Distillation

The washed reaction mixture is admixed with such an amount of storage stabilizer, preferably hydroquinone monomethyl ether, that, after removal of the solvent, 100-500 ppm, preferably 200-500 ppm and more preferably 200-400 ppm thereof are present in the target ester.

The majority of solvent is removed by distillation, for example, in a stirred tank with jacket heating and/or internal heating coils under reduced pressure, for example at 20-700 mbar, preferably from 30 to 500 mbar and more preferably from 50 to 150 mbar, and a temperature of 40-80° C.

It will be appreciated that the distillation can also be effected in a falling-film or thin-film evaporator. To this end, the reaction mixture, preferably repeatedly in circulation, under reduced pressure, is conducted through the apparatus, for example, at 20-700 mbar, preferably from 30 to 500 mbar, more preferably 50-150 mbar, and a temperature of 40-80° C.

Advantageously, an inert gas, preferably an oxygenous gas, more preferably air or a mixture of air and nitrogen (lean air) can be introduced into the distillation apparatus, for example 0.1-1 m$^3$/m$^3$h, preferably 0.2-0.8 m$^3$/m$^3$h and more preferably 0.3-0.7 m$^3$/m$^3$h, based on the volume of the reaction mixture.

The residual solvent content in the residue after distillation is generally below 5% by weight, preferably 0.5-5% by weight.

The solvent removed is condensed and preferably reused.

(Meth)acrylic acid and (meth)acrylic esters of $C_{17}$-alcohol mixtures are polymerizable compounds. Therefore, sufficient inhibition of polymerization should be ensured in all process steps. Undesired polymerization is a safety hazard owing to the large amount of heat released.

Therefore, in the process according to the invention, both the esterification reaction and the thermal separations are preferably carried out in the presence of customary amounts of polymerization inhibitors known per se. In general, based on the α,β-monoethylenically unsaturated monomers, per individual substance, from 1 to 10 000 ppm, preferably from 10 to 5000 ppm, more preferably from 30 to 2500 ppm and especially from 50 to 1500 ppm, of a suitable stabilizer are used.

Suitable stabilizers may, for example, be N-oxides (nitroxyl or N-oxyl radicals, i.e. compounds which have at least one >N—O.group), for example 4-hydroxy-2,2,6,6-tetramethylpiperidine N-oxyl, 4-oxo-2,2,6,6-tetramethylpiperidine N-oxyl, 4-acetoxy-2,2,6,6-tetramethylpiperidine N-oxyl, 2,2,6,6-tetramethylpiperidine N-oxyl, bis(1-oxyl-2,2,6,6-tetramethylpiperidin-4-yl)sebacate, 4,4',4"-tris(2,2,6,6-tetramethylpiperidine N-oxyl)phosphite or 3-oxo-2,2,5,5-tetramethyl-pyrrolidine N-oxyl; mono- or polyhydric phenols which may have one or more alkyl groups, for example alkylphenols, for example o-, m- or p-cresol (methylphenol), 2-tert-butylphenol, 4-tert-butylphenol, 2,4-di-tert-butylphenol, 2-methyl-4-tert-butylphenol, 2-tert-butyl-4-methylphenol, 2,6-tert-butyl-4-methylphenol, 4-tert-butyl-2,6-dimethylphenol or 6-tert-butyl-2,4-dimethylphenol; quinones, for example hydroquinone, hydroquinone monomethyl ether, 2-methylhydroquinone or 2,5-di-tert-butylhydroquinone; hydroxyphenols, for example pyrocatechol (1,2-dihydroxybenzene) or benzoquinone; aminophenols, for example p-aminophenol; nitrosophenols, for example p-nitrosophenol; alkoxyphenols, for example 2-methoxyphenol (guaiacol, pyrocatechol monomethyl ether), 2-ethoxyphenol, 2-isopropoxyphenol, 4-methoxyphenol (hydroquinone monomethyl ether), mono- or di-tert-butyl-4-methoxyphenol; tocopherols, for example α-tocopherol and 2,3-dihydro-2,2-dimethyl-7-hydroxybenzofuran (2,2-dimethyl-7-hydroxycoumaran), aromatic amines, for example N,N-diphenylamine or N-nitrosodiphenylamine; phenylenediamines, for example N,N'-dialkyl-p-phenylenediamine, where the alkyl radicals may be the same or different and each consist independently of from 1 to 4 carbon atoms and may be straight-chain or branched, for example N,N'-dimethyl-p-phenylenediamine or N,N'-diethyl-p-phenylenediamine, hydroxylamines, for example N,N-diethylhydroxylamine, imines, for example methyl ethyl imine or methylene violet, sulfonamides, for example N-methyl-4-toluenesulfonamide or N-tert-butyl-4-toluenesulfonamide, oximes, such as aldoximes, ketoximes or amide oximes, for example diethyl ketoxime, methyl ethyl ketoxime or salicyladoxime, phosphorus compounds, for example triphenylphosphine, triphenyl phosphite, triethyl phosphite, hypophosphorous acid or alkyl esters of phosphorous acids; sulfur compounds, for example diphenyl sulfide or phenothiazine; metal salts such as copper or manganese, cerium, nickel, chromium salts, for example chlorides, sulfates, salicylates, tosylates, acrylates or acetates, for example copper acetate, copper(II) chloride, copper salicylate, cerium (III) acetate or cerium(III) ethylhexanoate, or mixtures thereof.

The polymerization inhibitor (mixture) used is preferably at least one compound from the group of hydroquinone, hydroquinone monomethyl ether, phenothiazine, 4-hydroxy-2,2,6,6-tetramethylpiperidine N-oxyl, 4-oxo-2,2,6,6-tetramethylpiperidine N-oxyl, bis(1-oxyl-2,2,6,6-tetramethylpiperidin-4-yl)sebacate, 2-tert-butylphenol, 4-tert-butylphenol, 2,4-di-tert-butylphenol, 2-tert-butyl-4-methylphenol, 6-tert-butyl-2,4-dimethylphenol, 2,6-di-tert-butyl-4-methylphenol, 2-methyl-4-tert-butylphenol, hypophosphorous acid, copper acetate, copper(II) chloride, copper salicylate and cerium(III) acetate.

Very particular preference is given to using phenothiazine and/or hydroquinone monomethyl ether (MEHQ) as the polymerization inhibitor.

Preference is given to using the polymerization inhibitor (mixture) in the form of an aqueous solution.

To further support the stabilization, an oxygenous gas may be present, preferably air or a mixture of air and nitrogen (lean air).

In the process step of esterification, the oxygenous gas is preferably metered into the bottom region of the column and/or into a circulation evaporator.

The (meth)acrylates, prepared in accordance with the invention, of $C_{17}$-alcohol mixtures find use, for example, as monomers or comonomers in the preparation of dispersions which are used, inter alia, as adhesives, paints, or textile, leather and papermaking assistants.

In addition, the (meth)acrylates of $C_{17}$-alcohol mixtures prepared by the process according to the invention may find use as a comonomer in polymers, which are in turn used as an additive for fuel oils and lubricants and especially as a cold flow improver in fuel oils. Such a use is disclosed, for example, in European application EP 1 923 454 A1.

The example which follows is intended to illustrate the properties of the invention, but without restricting it.

Unless stated otherwise, percent always means percent by weight, and parts always parts by weight.

U.S. Provisional Patent Application No. 61/264,704, filed Nov. 27, 2009, is incorporated into the present patent application by literature reference. With regard to the abovementioned teachings, numerous changes and deviations from the present invention are possible. It can therefore be assumed that the invention, within the scope of the appended claims, can be performed differently than the way described specifically herein.

EXAMPLE

In an esterification apparatus (2 l 4-neck flask with internal thermometer, reflux condenser and water separator), the esterification of acrylic acid with a $C_{17}$ alcohol mixture was carried out. It was initially charged with 800 ml of cyclohexane, 513 g (2.0 mol) of heptadecanol (mean degree of branching of approx. 3.0) and 3.0 ml of stabilizer solution (1.25 g of hydroquinone monomethyl ether (MEHQ) and 3.25 g of hypophosphorous acid dissolved in 37.5 g of water) and 1.2 ml of 20% copper(II) chloride solution, and 180.3 g (2.5 mol) of acrylic acid (stabilized with 200 ppm of MEHQ) were added. The mixture was heated under an air atmosphere, and 9.6 ml of 98% methanesulfonic acid were added at an internal temperature of 75° C. After boiling under reflux for 2 hours, in the course of which water was removed continuously, the reaction solution was cooled.

240 ml of 7.5% sodium chloride solution were added to the resulting clear solution. 160 ml of 12.5% sodium hydroxide solution were used to establish a pH of 13. After extraction by shaking, the cyclohexane phase was removed and washed twice more with 240 ml each time of 7.5% sodium chloride solution, dried over sodium sulfate, filtered and admixed with 122 mg (200 ppm) of MEHQ. Subsequently, the solvent was removed under reduced pressure. A clear liquid was obtained.

Heptadecyl acrylate was obtained in a yield of 552.4 g (89%) and a purity of >95%, and with an APHA color number of 9.

The invention claimed is:

1. A process for preparing at least one (meth)acrylate of a $C_{17}$-alcohol mixture comprising:
   reacting (meth)acrylic acid with a $C_{17}$-alcohol mixture in the presence of at least one acidic catalyst and of at least one polymerization inhibitor and in the presence of a solvent which, with water, forms an azeotrope, wherein esterification is performed in a reactor with a circulation evaporator,
   the azeotrope is distilled off and condensed, and the condensate splits into an aqueous phase and an organic phase,
   the $C_{17}$-alcohol mixture has a mean degree of branching (iso index) of 2.8 to 3.7,
   the acidic catalyst is at least one selected from the group consisting of a mineral acid and a sulfonic acid, and
   the solvent is at least one selected from the group consisting of an aliphatic hydrocarbon, a cycloaliphatic hydrocarbon and an aromatic hydrocarbon.

2. The process according to claim 1, wherein the $C_{17}$-alcohol mixture has a mean degree of branching of 2.9 to 3.6.

3. The process according to claim 1, wherein the $C_{17}$-alcohol mixture has a mean degree of branching of 3.01 to 3.5.

4. The process according to claim 1, wherein the $C_{17}$-alcohol mixture has a content of alcohols having 17 carbon atoms of at least 95% by weight.

5. The process according to claim 1, wherein the polymerization inhibitor is at least one compound selected from the group consisting of hydroquinone, hydroquinone monomethyl ether, phenothiazine, 4-hydroxy-2,2,6,6-tetramethylpiperidine N-oxyl, 4-oxo-2,2,6,6-tetramethylpiperidine N-oxyl, bis(1-oxyl-2,2,6,6-tetramethylpiperidin-4-yl) sebacate, 2-tert-butylphenol,7 4-tert-butylphenol, 2,4-di-tert-butylphenol, 2-tert-butyl-4-methylphenol, 6-tert-butyl-2,4-dimethylphenol, 2,6-di-tert-butyl-4-methylphenol, 2-methyl-4-tert-butylphenol, hypophosphorous acid, copper acetate, copper(II) chloride, copper salicylate and cerium(III) acetate.

6. A (meth)acrylic ester prepared according to claim 1, wherein the solidification point (at atmospheric pressure) of the (meth)acrylic ester of the $C_{17}$-alcohol mixture is below 0° C.

7. A dispersion obtained from one or more (meth)acrylic esters according to claim 6, wherein the (meth)acrylic esters are the monomers or comonomers of said dispersion.

8. An adhesive, a paint, a textile, leather, a papermaking assistant, an additive for fuel oil, or an additive for lubricant, comprising the dispersion according to claim 7.

9. The process according to claim 1, wherein the $C_{17}$-alcohol mixture has a content of alcohols having 17 carbon atoms of more than 99.9% by weight.

* * * * *